United States Patent [19]

Siegmeier et al.

[11] Patent Number: 4,921,983

[45] Date of Patent: May 1, 1990

[54] METHOD FOR THE CONTINUOUS EPOXIDATION OF OLEFINS

[75] Inventors: Rainer Siegmeier, Bad Homburg; Willi Hofen, Rodenbach; Günter Prescher, Hanau; Helmut Maurer, Rodenbach, all of Fed. Rep. of Germany

[73] Assignee: Degussa Aktiengesellschaft, Frankfurt am Main, Fed. Rep. of Germany

[21] Appl. No.: 384,923

[22] Filed: Jul. 26, 1989

Related U.S. Application Data

[63] Continuation of Ser. No. 133,629, Dec. 16, 1987, abandoned.

[30] Foreign Application Priority Data

Dec. 18, 1986 [DE] Fed. Rep. of Germany ....... 3643207

[51] Int. Cl.$^5$ ............................................. C07D 30/14
[52] U.S. Cl. .................................................. 549/525
[58] Field of Search ................................. 549/525, 524

[56] References Cited

U.S. PATENT DOCUMENTS

| | | | |
|---|---|---|---|
| 3,663,574 | 5/1972 | Yamagishi et al. | 549/525 |
| 4,193,929 | 3/1980 | Hildon et al. | 549/525 |
| 4,424,391 | 1/1984 | Walralvens et al. | 549/525 |

*Primary Examiner*—Asok Pal
*Attorney, Agent, or Firm*—Cushman, Darby & Cushman

[57] ABSTRACT

In the continuous epoxidation of olefins with percarboxylic acids, the alkane component which normally accumulates during the circulation of the olefin is reduced by branching off a partial current from the recycled olefin and by additional epoxidation of this olefin with percarboxylic acids as well as a subsequent separation from the epoxide.

7 Claims, 1 Drawing Sheet

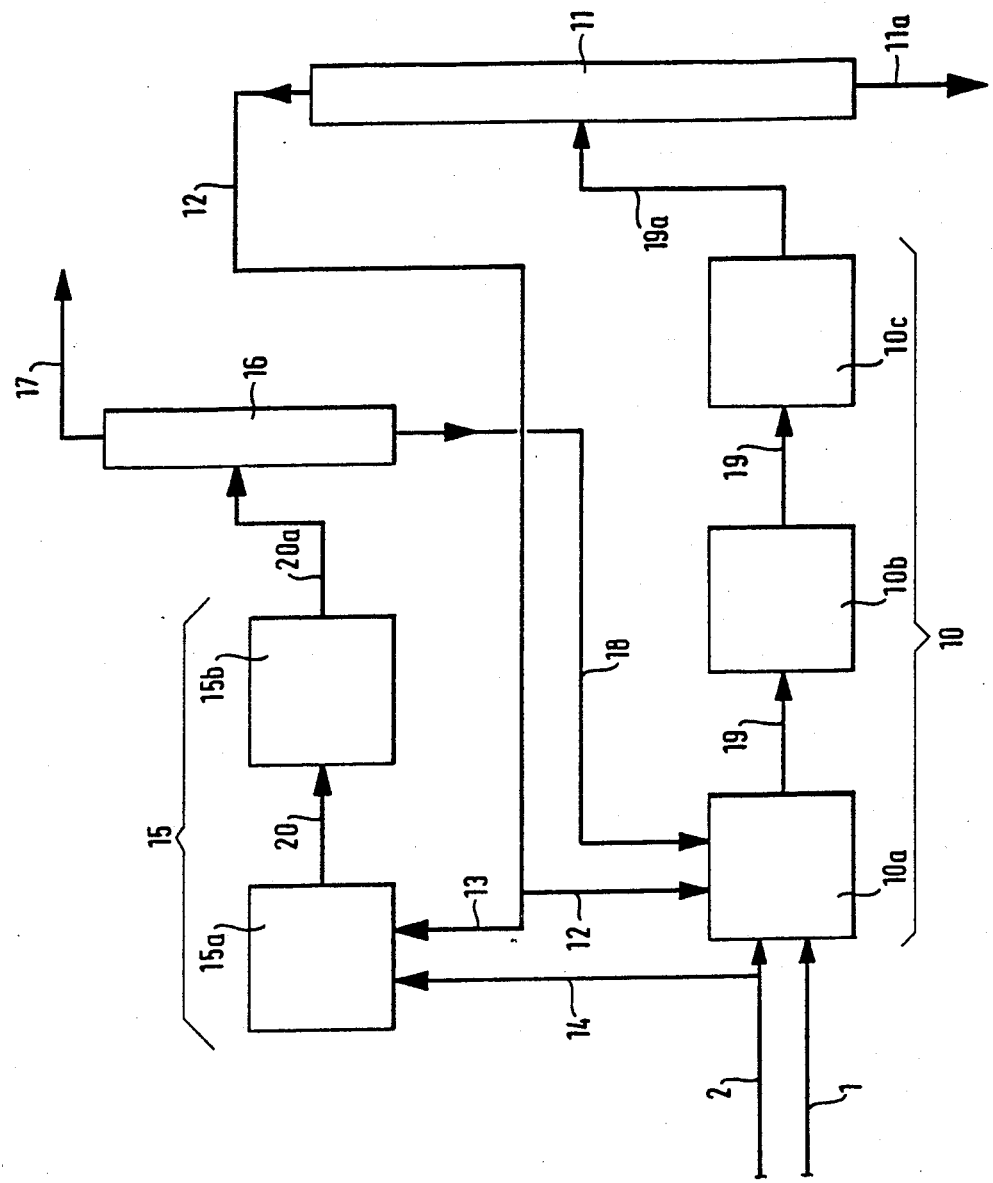

METHOD FOR THE CONTINUOUS EPOXIDATION OF OLEFINS

This is a continuation of application No. 133,629, filed Dec. 16, 1987, now abandoned.

The present invention relates to an improvement in continuous epoxidation of olefins with percarboxylic acids.

BACKGROUND OF THE INVENTION

Oxiranes which are produced in the epoxidation of olefins are useful as intermediary products, e.g. in the synthesis of diols, polyethers or polyurethanes, as well as in the production of paints.

The epoxidation of olefins with percarboxylic acids has been known for a long time, cf. D. Swern, "Organic Peroxides", Wiley Interscience, 1971, vol. II, pp. 360 ff. The percarboxylic acids used in that process can, to the extent that they are water-soluble, be used both as aqueous solutions and also in organic, essentially water-free solvents, cf. e.g. loc. cit., p. 375. Dispersions of non-water-soluble percarboxylic acids in water are not generally used.

Percarboxylic acids frequently used in industry are those with 2–4 carbon atoms such as peracetic acid, perpropionic acid and the perbutyric acids.

On the other hand, the performic acid which forms in situ is used less frequently than the higher-molecular percarboxylic acids because of the increased risk of corrosion, even when the reactor is made from a high-grade steel, and the decomposition which this causes, cf. German Patent Specification DE-AS No. 25 19 298 (corresponding to U.S. Pat. Nos. 4,113,747 and Re. 30,945).

Aromatic percarboxylic acids such as e.g. perbenzoic acid or monoperphthalic acid have also been used in olefin epoxidations, cf. German Patent Specification DE-OS No. 23 12 281. However, industrial use of these percarboxylic acids is not practical because of their cost.

The "olefins" which have been used include acyclic and cyclic aliphatic hydrocarbons of different chain lengths with one or several reactive double bonds.

These olefins also have been used as blends, that is, mixed with each other. This has been especially applicable to olefins containing more than 12 carbon atoms. Substituted olefins, e.g. halogenated olefins, have also been epoxidized with percarboxylic acids, cf. German Patent Specification DE-OS No. 27 34 243.

Epoxidations have been performed both discontinuously and also continuously. Since the olefins have generally been used in a more or less great excess in the continuous method in relation to percarboxylic acid, this excess has been recycled back into the epoxidation stage, cf. German Patent Specifications DE-OS No. 31 01 037 and DE-OS No. 34 42 937 (corresponding to U.S. Pat. No. 4,605,795).

In spite of known purification methods, commercially available olefins still contain, as is generally known, a certain residual amount of impurities. This residual amount of impurities consists of alkanes, primarily from monoolefins, whose boiling points are frequently very similar to those of olefins. This residual content of alkanes accumulates progressively in processes which involve recirculation, i.e., when the olefin charge is mixed with the recycled olefin, and thus it makes the entire process more difficult to carry out.

Separation of the alkanes by distillation of the recycled olefin is not always possible because of the similarity of the boiling points. Extractive distillations are too expensive in an epoxidation process, because of the additional expense for solvents.

The known chemical separation methods cannot be used since they are based e.g. on the separation of diolefins from monoolefins, but not on the separation of alkanes, cf. Ullmann, "Enzyclopaedie der technischen Chemie" [Encyclopedia of Industrial Chemistry], 3d edition, 1958, vol. 10, pp. 62–62.

SUMMARY OF THE INVENTION

The object of the present invention is to remove or reduce the amount of the inert components, primarily alkanes, which are present as admixtures in recycled olefins in epoxidation methods, without using chemicals not normally present in the reaction.

In accordance with the invention, it has been found that this object can be achieved if a part of the stream of olefin or olefin mixture which is circulated in the epoxidation and which contains the inert compounds, mainly alkanes, is removed from the main recirculated stream and epoxidized with a solution of percarboxylic acid. Then the mixture of epoxides and non-epoxidized inert components which is formed in this way is separated in a known manner. The epoxidized part of this partial stream may then be recirculated to the main epoxidation reaction.

It is preferable to use the same percarboxylic acid for epoxidizing the olefins contained in the partial stream which is also used in the main stream.

In principle, all percarboxylic acids used in epoxidation methods can be used in epoxidation of the partial stream in accordance with the method of the present invention: especially advantageous, however, are those with 2–4 carbon atoms, which are preferably used in organic solvents such as e.g. in aliphatic, cycloaliphatic or aromatic hydrocarbons such as pentane, 2-ethylhexane, cyclohexane, methylcyclopentane or benzene, toluene, tetralin or in ethers or esters such as tetrahydrofurane, ethyl propionate, ethyl acetate, butyl acetate or in chlorinated hydrocarbons such as methylene chloride, chloroform, carbon tetrachloride or dichloroethane, dichloropropane or chlorobenzene as well as the dichlorobenzenes. Mixtures of the solvents mentioned can also be used.

The concentrations of these percarboxylic acid solutions are generally between 5 and 50% by weight.

The reduction of the non-epoxidizible components in the recycled olefin or olefin mixture, in accordance with the present invention, can be used in all epoxidation methods which operate with an excess of olefin in relation to the percarboxylic acid and with a recycling of the non-converted olefin in the cycle.

This reduction of the non-epoxidizible components is preferably performed in such a manner that a set low level of these components is continuously maintained in the main olefin current. The size of the partial current to be removed and the amount of the percarboxylic acid to be used for this purpose depends preferably on the stationary concentration of the non-epoxidizible inert components which develops in the cycle current. This can be readily determined by a simple test.

The mixture of newly formed epoxides and non-epoxidizible components present after the completed epoxidation of the olefins in the partial stream may be separated in a known manner. Due to the epoxidation, the boiling-point difference between the epoxides and alkanes in relation to those of the olefins and alkanes has increased to such an extent that separation by means of a customary distillation and/or desorption is possible.

The method of the invention is advantageous in the continuous epoxidation of olefins which have a chain length of 3-12 carbon atoms, but it is useful with olefins having a greater chain length up to 20 carbon atoms. Epoxidation in accordance with the invention is especially advantageous in the case of olefins with 3-8 carbon atoms.

The epoxidation is performed with percarboxylic acids with 2-4 carbon atoms which are preferably present in the solvents cited on above. The concentration of the percarboxylic acids in the solvents cited is not critical but is preferably 10-30% by weight. Very advantageous solvents are benzene, toluene, cyclohexane, ethyl acetate, dichloropropane and chloroform. The method of the invention is especially well-suited for the epoxidation of pentene with a solution of perpropionic acid in benzene.

BRIEF DESCRIPTION OF FIGURE IN THE DRAWING

FIG. 1 is a schematic diagram illustrating the steps of the process of the invention.

DETAILED DESCRIPTION OF PREFERRED EMBODIMENTS

The process of the present invention will be better understood from the following description, in which reference is made to FIG. 1, and from the example which follows.

In schematic FIG. 1, reference numerals 10a, 10b and 10c signify three series-connected reactors for the main reaction 10, namely, the epoxidation of olefins with percarboxylic acids.

Reactors which can be used are e.g. agitated tank cascades or paddle reactors with flow tube connections at the outlet side.

An olefin or olefin mixture is introduced into system 10 via line 1 and the solution of percarboxylic acid, which can be either aqueous or in an organic solvent, is introduced into system 10 via line 2. The mixture from reactor 10a, which already partially consists of the reaction products, runs through reactors 10b and 10c via lines 19 and, in an almost completely reacted state, enters into processing apparatus 11, e.g. a distillation device, via line 19a. In this device, the excess olefin is separated together with alkane and fed via line 12 to the main reaction 10, e.g. to reactor 10a. Optionally the apparatus 11 may be combined with a desorption column. The reaction product leaves processing device 11 via line 11a.

According to the method of the invention, a part of the distilled mixture of olefin and alkane is removed from line 12 via line 13 and introduced into processing or prereaction system 15, which can consist of two reactors 15a and 15b connected in series. The reactor types mentioned above can also be used for this purpose. A branch current 14 of the percarboxylic acid solution flowing in via line 2 enters into reactor 15a. The mixture, which has already partially reacted, passes via line 20 into reactor 15b and as a essentially completely reacted mixture via line 20a into processing device 16. This device can be a distillation or stripper column, optionally combined with a desorption device. While the more volatile components, that is, a slight residual amount of olefin and the unreacted alkane. leave the system via line 17, the newly-formed epoxides flow via line 18 back to the main reaction 10. e.g. to reactor 10a.

EXAMPLE:

209 grams per hour of fresh pentene are supplied via line 1 (95.2% pentene, 4.8% pentane) and 848 grams per hour of a benzene solution of perpropionic acid (22% peracid) via line 2 to a continuously operated reaction system (main reaction 10)—see FIG. 1—consisting of two paddle reactors 10a, 10b and a flow tube 10c and fed into the first reactor 10a.

90 grams per hour recycled pentene is likewise supplied to the first reactor 10a of main reaction 10 from a circulation current 12 (75% pentene and 25% pentane) which is generated distillatively after the main reaction in column 11 from the reaction mixture.

The rest of circulation current 12—approximately 40 grams per hour—is supplied via line 13 to prereaction system 15 consisting of paddle reactor 15a and flow tube 15b (total dwell time 50 minutes) and reacted with 268 grams per hour of a benzene solution of perpropionic acid solution (perpropionic acid content 22% by weight) which is branched off via line 14 from main current 2 of the perpropionic acid solution. The reaction is carried out until 96% of the olefin component has completely reacted. The reaction mixture of prereactor 15 is subsequently distillatively freed in stripper column 16 at 300 mbar of the more volatile components pentene and pentane. Approximately 11 grams per hour of the more volatile components are obtained of which approximately 10 grams per hour is pentane. The runoff of stripper column 16 (297/h) flows to the first paddle reactor 10a of the main reaction via line 18. It contains the epoxide components reactively recovered from the partial current of the return pentene.

The total reaction mass (1444 grams per hour) flows through the main reaction 10a-10c with a dwell time of approximately 60 minutes and is subsequently processed by distillation. The recycled olefin (130 grams per hour) is produced which is fed in the manner described above as a partial stream to prereaction 15. Due to the partial current branched off in prereaction 15 and to the concentrated removal of pentane made possible after the complete reaction of the olefin component, the concentration of pentane in the total circuit current is in steady state equilibrium (approximately 25%). All percents are weight percents.

What is claimed is:

1. In a continuous method for the epoxidation of one or more olefins containing inert components, primarily alkanes with a percarboxylic acid which is present in aqueous solution or in an organic solvent in a reactor and in which method the olefins are used in excess in relation to the percarboxylic acid and the non-converted olefin component which contains inert components, primarily alkanes, is recirculated.

the improvement for removing or reducing the amount of inert components, primarily alkanes, which are present as admixtures in the recycled olefins, without using chemicals not normally present in the reaction, said improvement comprising separating a partial stream from the recirculating olefin, essentially completely epoxidizing the unreacted olefins in the partial stream with a solution of percarboxylic acid, separating the resulting epoxidized product from any unreacted olefins and the inert components in said epoxidized partial stream and introducing the epoxidized product from said partial stream without the inert components therein into the reactor.

2. A method as set forth in claim 1 in which the epoxidized product is separated from the recirculating stream before separating the partial stream.

3. A method as set forth in claim 1 or claim 2 including returning the epoxidized product separated from the epoxidized partial stream to the main epoxidation reaction of percarboxylic acid and olefin.

4. A method according to claim 1 in which the same percarboxylic acid is used in the main epoxidation reaction and in the epoxidation of the partial stream.

5. A method according to claim 1 or claim 4 in which the percarboxylic acid contains 2-4 carbon atoms.

6. A method according to claim 1 or claim 4 in which the percarboxylic acid is used in a solution in benzene.

7. A method according to claim 1 or claim 4 in which the olefin is pentene and the main epoxidation and the epoxidation of the partial stream are carried out with a benzene solution of perpropionic acid.

* * * * *